US010633678B2

(12) United States Patent
Streekstra et al.

(10) Patent No.: US 10,633,678 B2
(45) Date of Patent: *Apr. 28, 2020

(54) PREPARATION OF MICROBIAL OIL

(71) Applicant: DSM IP Assets B.V., Te Heerlen (NL)

(72) Inventors: Hugo Streekstra, Amsterdam (NL);
Petrus Joseph Maria Brocken, De Lier (NL)

(73) Assignee: DSM IP ASSETS B.V., Te Heerlen (NL)

( * ) Notice: Subject to any disclaimer, the term of this patent is extended or adjusted under 35 U.S.C. 154(b) by 327 days.

This patent is subject to a terminal disclaimer.

(21) Appl. No.: 14/027,588

(22) Filed: Sep. 16, 2013

(65) Prior Publication Data
US 2014/0017742 A1    Jan. 16, 2014

Related U.S. Application Data

(60) Continuation of application No. 12/242,997, filed on Oct. 1, 2008, now abandoned, which is a division of application No. 10/518,949, filed as application No. PCT/EP03/06552 on Jun. 20, 2003, now Pat. No. 7,470,527.

(30) Foreign Application Priority Data

Jun. 19, 2002 (EP) .................... 02254262
Dec. 18, 2002 (EP) .................... 02258713
Feb. 26, 2003 (EP) .................... 03251169

(51) Int. Cl.
| C12P 7/64 | (2006.01) |
| A23L 33/12 | (2016.01) |
| A23K 20/158 | (2016.01) |
| A23D 9/00 | (2006.01) |
| A23L 33/115 | (2016.01) |
| C12N 1/00 | (2006.01) |
| A61Q 19/00 | (2006.01) |
| A61K 8/92 | (2006.01) |
| A61K 8/67 | (2006.01) |
| C11B 1/10 | (2006.01) |
| A23D 9/02 | (2006.01) |
| A61K 8/99 | (2017.01) |

(52) U.S. Cl.
CPC .............. *C12P 7/6472* (2013.01); *A23D 9/00* (2013.01); *A23D 9/02* (2013.01); *A23K 20/158* (2016.05); *A23L 33/115* (2016.08); *A23L 33/12* (2016.08); *A61K 8/67* (2013.01); *A61K 8/925* (2013.01); *A61K 8/99* (2013.01); *A61Q 19/00* (2013.01); *C11B 1/10* (2013.01); *C12N 1/005* (2013.01); *C12P 7/6427* (2013.01); *C12P 7/6481* (2013.01); *A61K 2800/85* (2013.01)

(58) Field of Classification Search
None
See application file for complete search history.

(56) References Cited

U.S. PATENT DOCUMENTS

| 5,128,250 | A | 7/1992 | Akimoto et al. |
| 5,322,780 | A | 6/1994 | Kawashima et al. |
| 5,882,703 | A | 3/1999 | Barclay |
| 6,746,857 | B2 | 6/2004 | Higashiyama et al. |
| 7,470,527 | B2 | 12/2008 | Streekstra et al. |
| 2002/0037561 | A1* | 3/2002 | Barclay .................. A61K 35/68 435/134 |
| 2005/0202148 | A1 | 9/2005 | Streekstra et al. |
| 2009/0053342 | A1 | 2/2009 | Streekstra et al. |

FOREIGN PATENT DOCUMENTS

| CN | 1362522 A | 12/2001 |
| EP | 0223960 A2 | 6/1987 |
| EP | 1 035 211 | 9/2000 |
| JP | 64-38007 | 2/1989 |
| JP | 2-13388 | 1/1990 |
| JP | 02013388 | 1/1990 |
| JP | 2-142486 | 5/1990 |
| JP | 02142486 | 5/1990 |
| JP | 10-512444 | 12/1998 |
| WO | WO 92/13086 | 8/1992 |

(Continued)

OTHER PUBLICATIONS

Hempenius et al., Food and Chemical Toxicology, 35:573-581, 1997.*

(Continued)

*Primary Examiner* — Allison M Fox
*Assistant Examiner* — Qing Xu
(74) *Attorney, Agent, or Firm* — Shannon McGarrah; Xi Chen

(57) ABSTRACT

The present invention provides a process for the production of a microbial oil comprising culturing a micro-organism in a two stage fermentation process where, in a last stage that precedes the end of fermentation, the carbon source is: consumed by the micro-organisms at a rate greater than it is added to the medium; added at a rate #0.30 M carbon/kg medium; or is rate limiting on the growth of the microorganism. The micro-organisms thus have the carbon source restricted so that they preferentially metabolise fats or lipids other than arachidonic acid (ARA), so increasing the proportion of ARA in the cells. A microbial oil is then recovered from the micro-organism, using hexane as a solvent, that has at least 50% ARA and at least 90% triglycerides.

18 Claims, No Drawings

(56) References Cited

FOREIGN PATENT DOCUMENTS

| WO | WO 96/21037 | 7/1996 |
| WO | WO1996021037 | 7/1996 |
| WO | WO 97/37032 | 10/1997 |
| WO | WO 02/10322 | 2/2002 |

OTHER PUBLICATIONS

Eroshin et al, "Arachidonic acid production by *Mortierella alpina* with growth-coupled lipid synthesis", Process Biochemistry (2000) 35:1171-1175.

International Search Report for PCT/EP03/06552, dated Mar. 9, 2005, 5 pages.

Jang Hung-Der et al, "Polyunsaturated fatty acid production with *Mortierella alpina* by solid substrate fermentation", Botanical Bulletin of Academia Sinica (2000) 41(1):41-48.

Lindberg et al, "Effect of temperature and glucose supply on the production of polyunsaturated fatty acids by the fungus *Mortierella alpina* CBS 343.66 in fermentor cultures", Applied Microbiology and Biotechnology (1993) 39:450-455.

Shimizu, "Production of $C_{20}$ Polyunsaturated Fatty Acids by Microbial Processes", Oils-Fats-Lipids 1995, Proc. World Congr. Int. Soc. Fat Res., $21^{st}$ (1996), Meeting Date 1995, vol. 1 pp. 103-109.

Totani et al, "Industrial Production of Arachidonic Acid by *Mortierella*", Chapter 4 in Industrial Applications of Single Cell Oils (ed. by D.J. Kyle and C. Ratledge), American Oil Chemists' Society, Champaign, Illinois (1992), pp. 52-60.

Totani et al, Lipids (1987) 22(12):1060-1062.

Yamada et al, "Production of Dihomo-Gamma-Linolenic Acid, Arachidonic Acid and Eicosapentaenoic Acid by Filamentous Fungi," in Industrial Applications of Single Cell Oils (ed. by D.J. Kyle and C. Ratledge), American Oil Chemists' Society, Champaign, Illinois (1992), pp. 118-138.

Shinmen et al, "Production of arachidonic acid by *Mortierella* fungi", Applied Microbiology and Biotechnology (1989) 31:11-16.

Shimizu et al, "Production of Eicosapentaenoic Acid by *Mortierella* Fungi", JAOCS, 65(9):1455-1459, 1988.

Eroshin et al, "Arachidonic acid production by *Mortierella alpina* with growth-coupled lipid synthesis", Process Biochemistry, 35:1171-1175, 2000.

Shinmen et al, "Production of arachidonic acid by *Mortierella* fungi", Appl Microbiol. Biotechnol. 31:11-16, 1989.

Higashiyama et al, "Effects of Mineral Addition on the Growth Morphology of and Arachidonic Acid production by Mortierella alpina 1 S-4", JAOCS 75, 1815-1819 (1998).

Higaghiyama et al., Production of Arachidonic acid by *Mortierella* Fungi, Biotechnol. Bioprocess Eng., 2002, 252-262, 7.

Higashiyama et al., Enhancement of Arachidonic Acid Production by Mortierella alpina 1S-4, JAOCS, 1998, 1501-1505, 75(11).

Totani et al., The Filamentous Fungus *Mortierella alpina*, High in Arachidonic Acid, Lipids, 1987, 1060-1062, 22(12).

\* cited by examiner

US 10,633,678 B2

PREPARATION OF MICROBIAL OIL

RELATED APPLICATIONS

This is a continuation of application Ser. No. 12/242,997 (pending), filed Oct. 1, 2008 (published as US2009-0053342 A1), which is a divisional of application Ser. No. 10/518, 949, filed Dec. 17, 2004 (issued as U.S. Pat. No. 7,470,527), which is a U.S. national phase of PCT/EP2003/006552, filed Jun. 20, 2003, which claims benefit of European Applications 03251169.3, filed Feb. 26, 2003, 02258713.3, filed Dec. 18, 2002 and 02254262.5, filed Jun. 19, 2002, the entire contents of each of which is hereby incorporated by reference in this application.

FIELD OF THE INVENTION

The present invention relates to a process for the production of a PUFA, optionally in a microbial oil, comprising culturing a micro-organism in a two-stage process and subsequently recovering the microbial oil from the micro-organisms. The invention also relates to a novel (e.g. microbial) oil resulting from such a process. In the oil 50% or more of the lipids (or PUFAs, such as in the oil) are arachidonic acid (ARA). The oil may have a low peroxide value (POV), of below 2.5 or 2.0 and/or a low anisidine value (AnV), below 1.0. The present invention also relates to foodstuffs and food supplements comprising, or generated using, the microbial oil of the invention.

INTRODUCTION

Polyunsaturated fatty acids, or PUFAs, are found naturally. A wide variety of different PUFAs are produced by different single cell organisms (algae, fungi, etc). One particularly important PUFA is arachidonic acid (ARA), one of a number of Long Chain Poly-Unsaturated Fatty Acids (LC-PUFAs). Chemically, arachidonic acid is cis-5,8,11,14 eicosatetraenoic acid (20:4) and belongs to the (n-6) family of LC-PUFAs.

Arachidonic acid is a major precursor of a wide variety of biologically active compounds, known collectively as eicosanoids, a group comprising prostaglandins, thromboxanes and leukotrienes. Arachidonic acid is also one of the components of the lipid fraction of human breast milk and is thought to be essential for optimal neurological development in infants. Arachidonic acid has a wide variety of different applications including use in infant formula, foodstuffs and animal feeds.

Arachidonic acid can be produced using micro-organisms and in particular using the filamentous fungi *Mortierella*. However, the percentage of arachidonic acid in the microbial oil produced is usually too low. A number of attempts have been made to try and increase the yield of arachidonic acid from *Mortierella*, but with varying degrees of success. Many of the attempts to increase arachidonic acid levels have involved steps that cannot be readily used in an industrial setting.

For example, Eroshin et al, Process Biochemistry: (35) 2000, pp 1171-1175 leaves the culture to sit for a period of about a week after the end of fermentation. The amounts of ARA quoted are based on the biomass (and not on oil extracted from it) as this document does not describe the extraction of any oil. Totani et al, Industrial Applications of single cell oils, American Oil Chemists' Society Campaign, 1992, Chapter 4, pp 52-60 and Lipids, vol. 22 No. 12 (1987) pages 1060-1062 advocates the use of an unusually low fermentation temperature which means the fermentation is considerably slowed. The ARA content here is based on extraction with a chloroform/methanol solvent mixture. Another document in the ARA production field is WO 96/21037.

EP-A-1035211 (Suntory) describes a process for producing ARA and DHGLA lipids from *M. alpina*. However, the calculation of ARA content is based either on the biomass (rather than an oil extracted from it), or results from an analytical method where the polyunsaturated fatty acids are esterified first, and then extracted using a solvent (rather than being extracted first, to produce an oil, and the ARA content then being determined on the basis of this oil).

One report of a higher yield of ARA alleges a concentration in harvested mycelia of nearly 70% using the strain 1S-4 of *M. alpina* (Shimizu S., Oils-Fats-Lipids 1995, Proc. World Congr. Int. Soc. Fat Res., $21^{st}$ (1996), Meeting Date 1995, Volume 1, pages 103-109 and Biochemical and Biophysical Research communications, Vol. 150(1), 1988, pages 335-441). However this percentage is based on the cells, and is not the same as the ARA percentage in a microbial oil. In fact the oil made only gave an ARA content of 39.0% (Table 27.2, page 105). (Note that the art uses a variety of different ways to measure ARA content, which may not necessarily be the same unit or based on the same analytical protocol as the FIGURES quoted later in this specification). Furthermore, this was only obtained when the *M. alpina* cells were allowed to stand at room temperature for a further 6 days after fermentation, which is clearly not a viable option for industrial production processes.

There is, therefore, a need to identify ways to increase the proportion (and so yield) of arachidonic acid in the microbial oils and in particular in a way that can be employed on an industrial scale.

SUMMARY OF THE INVENTION

The present invention provides novel processes to produce a (microbial) oil with an increased proportion of arachidonic acid. This means arachidonic acid may be produced at a reduced cost and increased rate. In addition, as the present invention does not rely on the genetic modification of micro-organisms involved in order to enhance arachidonic acid production, the invention can help to meet the increasing demand for natural, non-genetically modified food ingredients. In addition the oil has low oxidation potential and so is suitable for incorporation into human foods for which toxicity is particularly important, such as infant formula.

Accordingly, a first aspect of the invention relates to a process for the production of a microbial oil or a polyunsaturated fatty acid (PUFA). The process comprises fermenting (or culturing) a micro-organism inside a fermentation vessel, suitably in a culture medium, whereby before (or at a stage which precedes) the end of fermentation;
  a) the carbon source is consumed by the micro-organisms at a rate greater than it is added to the medium;
  b) the carbon source is added at a rate of #0.30M carbon/kg medium per hour;
  c) the carbon source is rate limiting on the growth of the micro-organisms, or is restricted such that the micro-organisms metabolise (its own) fat(s) and/or lipid(s);
  d) the rate of addition of the carbon source is reduced to, or is below, the rate of consumption of the carbon source by the micro-organisms;

e) the carbon source has been all used, or has a concentration in the medium of about zero, at or before the end of fermentation;
f) the carbon source addition is stopped but fermentation is allowed to continue; and/or
g) the micro-organisms are subjected to conditions such that they metabolise fat(s) (e.g. inside the cell, such as a PUFA) other than ARA in preference to ARA.

A second aspect of the present invention relates to a microbial oil which comprises at least 50% (or at least 50.5, 51 or 52%) arachidonic acid (ARA). It may have up to 55, 57 or 60% ARA. This oil may have:
a) a triglyceride content of at least 90%;
b) a POV of less than 2.5;
c) an AnV of less than 1.0; and/or
d) a phospholipid content below 5%.

The oil can be preparable by the process of the first aspect. It may be hexane extracted.

It is thought that once the concentration of carbon source is reduced or restricted, the cells start metabolising the fats or lipids inside the cell. However, the cells consume fats other than ARA first. In this way the proportion of ARA in the fats or lipids in the cells increases. Hence the process of the first aspect can, in this way, lead to a higher ARA content oil of the second aspect.

DETAILED DESCRIPTION OF THE INVENTION

Micro-Organisms

The micro-organism employed may be a bacteria, yeast, algae or fungus. Preferably a fungus is used and in particular a filamentous fungus is used. Preferred fungi are of the order Mucorales. The fungus may be of the genus *Mortierella, Phycomyces, Entomophthora, Pythium, Thraustochytrium, Blakeslea, Rhizomucor* or *Aspergillus*. Preferred fungi are of the species *Mortierella alpina*. Preferred yeasts are of the genus *Pichia* or *Saccharomyces*, for example *Pichia ciferrii*. Bacteria can be of the genus *Propionibacterium*. Suitable algae are dinoflagellate and/or belong to the genus *Crypthecodinium, Porphyridium* or *Nitschia*, for example are of the species *Crypthecodinium cohnii*.

The micro-organism strains used in the present invention may be a naturally occurring or commonly used industrial strain. The strain may not have been genetically altered for example, it may not be transformed with a vector nor may it contain heterologous gene(s). Given the current preference in some quarters for foodstuffs which do not contain genetically engineered ingredients, the micro-organism employed may be a strain which has not been so modified.

Polyunsaturated Fatty Acids (PUPAS)

The PUFA can either be a single PUFA or two or more different PUFAs.

The or each PUFA can be of the n-3 or n-6 family. Preferably it is a C18, C20 or C22 PUFA. It may be a PUFA with at least 18 carbon atoms and/or 3 or 4 double bonds. The PUFA(s) can be isolated in the form of a free fatty acid, a salt, as a fatty acid ester (e.g. methyl or ethyl ester), as a phospholipid and/or in the form of a mono-, di- or triglyceride.

Suitable (n-3 and n-6) PUFAs include:
docosahexaenoic acid (DHA, 22:6 E23), suitably from algae or fungi, such as the (dinoflagellate) *Crypthecodinium* or the (fungus) *Thraustochytrium*;
γ-linolenic acid (GLA, 18:3 Ω6);
α-linolenic acid (ALA, 18:3 Ω3);
conjugated linoleic acid (octadecadienoic acid, CLA);
dihomo-γ-linolenic acid (DGLA, 20:3 Ω6);
arachidonic acid (ARA, 20:4 Ω6); and
eicosapentaenoic acid (EPA, 20:5 Ω3).

Preferred PUFAs include arachidonic acid (ARA), docosohexaenoic acid (DHA), eicosapentaenoic acid (EPA) and/or γ-linoleic acid (GLA). In particular, ARA is preferred.

Fermentation

The fermentation/culturing will typically be carried out in a suitable fermenter (or fermentation vessel) containing a (liquid, usually aqueous) culture medium. A main fermenter vessel will normally be aseptically inoculated from a small feed fermenter. Typically a submerged and/or aerobic fermentation process is employed. This may take place in a deep tank fermenter. The fermenter may be equipped with devices to monitor and/or change pH and temperature. The vessel may additionally be adapted to perform, or allow to be conducted, aeration and/or mixing of the cells and liquid, such as agitation of the solution. This may be stirring, for example achieved using mechanical means.

Suitably the volume of the fermenter is at least 10, 20, 40 or even 60 $m^3$. Volumes as high as 100 or even 150 $m^3$ can be used.

The fermentation will typically last for 10 days or less, preferably 9 or less days, more preferably 8 or less days. It may be at least 4, 5, 6 or 7 days.

Optionally the fermentation may be for 150 to 200 hours, such as 160 to 190 hours, eg. from 170 to 180 hours. The end of fermentation is usually the point at which agitation and/or aeration is stopped. This can be when the fermenter vessel, and/or ancillary equipment, is (effectively) switched off. The micro-organisms may then be removed from the fermenter.

The fermentation may be at a temperature of from 20 to 40° C.

Carbon and Nitrogen Sources

Any suitable medium may be used in the fermentation, for example a medium appropriate to the micro-organism being used. The carbon source can comprise (complex sources such as) maltodextrin, oat flour, oat meal, molasses, vegetable (e.g. soy bean) oil, malt extract, starch, ethanol or soy bean oil. Preferred (non-complex) carbon sources include carbohydrates or sugars, such as fructose, maltose, sucrose, xylose, mannitol, glucose or lactose or glycerine (e.g. from a vegetable source), citrate, acetate, glycerol, ethanol or (e.g. sodium) ascorbate. In a preferred embodiment of the invention the carbon source is or comprises glucose, and in particular is glucose syrup.

Suitable nitrogen sources include yeast extract, urea and peptone. The medium can exclude agar.

Preferred nitrogen and/or carbon sources are water soluble or water miscible.

Individual components of the medium (such as the nitrogen and/or carbon sources) may either (all) be present at the start of fermentation, added continuously during fermentation or added in stepwise or batches. In particular, the amount of carbon source present in the medium will typically be controlled as described below, preferably by controlling the rate of addition of the carbon source.

The nitrogen and/or carbon sources can be supplied (or added) separately, or supplied simultaneously, or supplied as a combined preparation. They may thus present in the same composition (if thought necessary) which is preferably a liquid. The carbon and/or nitrogen sources can be added (to the fermenter vessel) either before the fungal cells are added (to the vessel), in other words prior to inoculation, or during fermentation alternatively they may be added both before fermentation and during.

Culture Medium

The culture medium is preferably an aqueous liquid. This may additionally contain other substances to assist in the fermentation, for example a chelating agent (e.g. citric acid), an anti-foaming agent (e.g. soy bean oil), a vitamin (e.g. thiamine and/or riboflavin), any necessary catalytic metals (for example, alkali earth metals such as magnesium or calcium, or zinc or iron and/or other metals such as cobalt and copper), phosphorus (e.g. phosphate) and/or sulphur (e.g. sulphate). The medium may, if necessary, contain an additive oil such as olive or soybean oil, however preferably the medium does not contain such an oil.

The (optimum) growth (or fermentation) temperature may vary depending on the micro-organism used. However, it is preferably from 20 to 40° C. and more preferably from 22 to 30 or 32° C. In particular the temperature the fermentation is carried out at will be ≥22° C. or ≤25° C., eg. 22 to 30° C., such as from 23-28° C. The pH of the aqueous liquid during fermentation may be from 4 to 10, such as from 5 to 8, optimally from 6 to 7.

The medium will typically be stirred or agitated during fermentation to help facilitate aeration. The aqueous liquid and the cells are suitably either mixed or agitated. This may be achieved if aeration is provided, such as by bubbling a gas, e.g. air, into the aqueous liquid. This may serve the additional purpose of providing oxygen to the fungal cells: hence the fermentation is preferably an aerobic one. Other means of agitation or mixing include stirring, for example using an impeller. This may be of a hydrofoil axial flow design or may be designed so that the aqueous medium is forced radially outwards from the impeller (such as a turbine). Even if there is no stirring it is preferred that the microbial cells are provided with oxygen during fermentation, and so aeration (e.g. by bubbling air, oxygen or other oxygen-containing gas) is advantageous here. Aeration may be at from 0.1 to 2.0, such as from 0.5 to 1.0 vvm.

Preferably the volume of the fermenter is at least 2 or 5 litres, preferably at least 10 litres. However, for fermenters used in industry, or on an industrial scale, the vessel volume is preferably at least 50, 100, 500 or 1,000 litres.

Last (or Second) Stage of Fermentation

The fermentation process may be split into at least two stages. A second or last stage, which may immediately precede the end of fermentation, can be characterised by a decrease in the amount of the carbon source available to the micro-organism or any of the features (a) to (g) as given in the first aspect. Typically, this stage can begin from 15 to 2 hours before the end of fermentation, preferably less than or at 10 hours from the end of fermentation, more preferably from 3 to 5 hours from the end of fermentation. Preferably, this stage will typically begin less than 10 days after the beginning of fermentation, more preferably it will begin less than 9 days after, even more preferably less than 8 days after.

During a first or earlier stage of fermentation the carbon source may be in excess. Thus the amount of carbon source available may not be limiting to on the growth of the micro-organisms. The rate of addition of the carbon source may exceed the rate of its consumption by the micro-organisms. In the second or last stage of fermentation the amount of the carbon source being added can be decreased or stopped altogether. This means that the amount of carbon source available to the micro-organism will decrease during the second or last stage of fermentation. Typically in a second, final or last stage, or towards the end of fermentation, the carbon source can be:

consumed by the micro-organisms at a rate greater than it is added to the medium (for example the rate of addition is less than the rate of consumption);

added at a rate #0.30 M carbon/kg medium per hour, such as #0.25 or #0.20, but at least 0.01, 0.02 or 0.05 M carbon/kg medium/hr (the units here referring to the moles, or molar amount, of carbon in the carbon source, rather than the weight or moles of the carbon source itself);

rate limiting on the growth and/or (PUFA) production of the micro-organisms.

Typically, the concentration of the carbon source during the second stage is #10 g carbon source/kg of medium, preferably from 0.01 or 0.1 to 8 or 10 g/kg, more preferably from 0.5 to 5 g/kg and even more preferably from 1 or 2 to 4 or 5 g/kg. This means that, on average during the last stage of fermentation, there will be #0.30M carbon per kg of medium, preferably from 0.003 M to 0.3M carbon per kg. Advantageously this is from 0.015M to 0.17M carbon per kg and even more preferably from 0.03M to 0.17M carbon per kg.

When the carbon source comprises glucose, typically the concentration of glucose (in the last stage) will be on average #10 g/kg of medium, preferably from 0.01 or 0.1 to 8 or 10 g/kg. Advantageously this is from 0.5 to 5 g/kg and even more preferably from 1 or 2 to 4 or 5 g/kg medium. In this sense medium includes the cells and the aqueous culture medium, that is to say it is the "broth" (cells and surrounding liquid).

The rate of addition of the carbon source in the last stage is preferably no more than 0.03M carbon per kg, preferably no more 0.025 or 0.02 M carbon per/kg (medium). Preferably the rate of addition is about 0.015M carbon per/kg. If the carbon source is glucose, then preferably the rate of addition of glucose is less than 1.0, for example less than 0.8, for example less than 0.5 g glucose per/kg medium per hour.

Preferably the rate of addition of the carbon source in the last stage is approximately half that of the rate of consumption of the carbon source by the micro-organisms. However, the ratio of rate of addition: rate of consumption may vary from 1:1-3, such as from 1:1.5 to 2.5, optimally from 1:1.8 to 2.2. Alternatively, the rate of addition may be from 30-70%, such as from 40 to 60%, optimally from 45 to 55%, of the rate of consumption.

The appropriate concentration of the carbon source during the second stage of the fermentation can be achieved by carefully controlling the rate of addition of the carbon source. Typically, this will be decreased as appropriate during, or to precipitate the onset of the last stage. Periodic sampling and analysis of the culture can be used to determine the concentration of the carbon source and to make adjustments as necessary to the rate of addition of the carbon source. This may be done automatically using a computer system.

Pasteurisation Process

Pasteurisation will usually take place after fermentation has finished. In a preferred embodiment, pasteurisation will finish the fermentation, because the heat during pasteurisation will kill the cells. Pasteurisation may therefore be performed on the fermentation broth (or the cells in the liquid (aqueous) medium), although it can be performed on the microbial biomass obtained from the broth. In the former case, pasteurisation can take place while the microbial cells are still inside the fermenter. Pasteurisation preferably takes place before any further processing of the microbial cells, for example granulation (e.g. by extrusion) crumbling, or kneading.

Preferably the pasteurisation protocol is sufficient to inhibit or inactivate one or more enzymes that can adversely affect or degrade a PUFA or microbial oil, for example a lipase.

Once fermentation has been finished, the fermentation broth may be filtered, or otherwise treated to remove water or aqueous liquid. After water removal, one may obtain a biomass "cake". If pasteurisation has not taken place, then the dewatered cells (or biomass cake) can be subjected to pasteurisation.

Oil Extraction

If desirable, and for example after fermentation is finished, the micro-organisms may be killed or pasteurised. This may be to inactivate any undesirable enzymes, for example enzymes that might degrade the oil or reduce the yield of the PUFAs.

After culturing or fermentation is complete or has ended, the fermentation broth (cells and aqueous liquid) may then be removed from the fermenter, and if necessary liquid (usually water) removed therefrom. Any suitable solid liquid separation technique can be used. This (dewatering) may be by centrifugation and/or filtration. The cells may be washed, for example using an aqueous solution (such as water) for example to remove any extracellular water-soluble or water-dispersible compounds. An oil can then be recovered from the microbes, for example using a solvent so that the oil may be solvent-extracted, preferably hexane-extracted.

The oil may have no (or be substantially free from) GLA and/or DGLA.

PUFA Extraction Process

The PUFA (or microbial oil, usually containing the PUFA) may be extracted from (e.g. dried) granules (e.g. extrudates) containing the cells. The extraction can be performed using a solvent. Preferably a non-polar solvent is used, for example a $C_{1-8}$, e.g. $C_{2-6}$, alkane, for example hexane. One may use carbon dioxide (in a liquid form, for example in a super critical state).

The cells may thus be subjected to extraction, such as with an organic solvent, preferably under nitrogen flow. Other usable organic solvents include ether, methanol, ethanol, chloroform, dichloromethane and/or petroleum ether. Extraction with methanol and petroleum ether and/or extraction with a one-layer solvent system consisting of chloroform, methanol, and water can also be used. Evaporation of the organic solvent(s) from the extract under reduced pressure can give a microbial oil containing arachidonic acid at a high concentration.

Preferably, the solvent is allowed to percolate over the dried granules. Suitable micro-organism granulation and extrusion techniques and subsequent extraction of a microbial PUFA containing oil, are described in WO-A-97/37032.

The solvent allows one to obtain a crude PUFA containing oil. This oil can be used in that state, without further processing, or it can be subjected to one or more refining steps. Suitable refining protocols are described in International patent application no. PCT/EP01/08902 (the contents of this document and all others described herein arc hereby incorporated by reference). For example, the oil can be subjected to acid treatment or degumming, alkali treatment or free fatty acid removal, bleaching or pigment removal, filtration, winterisation (or cooling, for example to remove saturated triglycerides), deodorising (or removal of free fatty acids) and/or polishing (or removal of oil-insoluble substances).

The resulting oil is particularly suitable for nutritional purposes, and can be added to (human) foods or (animal) feedstuffs. Examples include milk, infant formula, health drinks, bread and animal feed.

Purification/Refinement

The microbial oil may be refined and purified. This may involve removing one or more of the following components: a phospholipid, trace metal, pigment, carbohydrate, protein, free fatty acid (FFA), oil insoluble substance, water insoluble substance, soap or saponified substance, oxidation product, sulphur, mono- or diglyceride, pigment decomposition product, solvent and/or sterol. The purifying may reduce or remove "off-flavours" and/or improve the stability of the oil.

To effect this the process (e.g. purifying) may comprise degumming (or acid treatment), neutralization (or alkali treatment), water washing, bleaching, filtering, deodorising, polishing and/or cooling (or winterization). Preferably the purifying comprises acid treatment and/or alkali treatment (degumming and neutralisation). Alternatively purifying methods may comprise bleaching and/or deodorization. Preferably however the purifying will involve bleaching and/or deodorization, and optimally in addition acid and/or alkali treatment.

Oils

The second aspect of the present invention provides a microbial oil which comprises 35 or 40% of at least one PUFA, such as ARA. The oil can have at least 50, 55 or 60% or more of this PUFA, such as ARA. It can have triglyceride content of at least 90%. Preferably the microbial oil comprises from 50, 55 or 60 to 90% arachidonic acid, more preferably from 60 to 80% and even more preferably from 60 to 70% arachidonic acid.

Preferably the microbial oil has a triglyceride content of from 90 to 100%, such as at least 90 or 96%, preferably at least 98%, more preferably at least 99% and optimally above 99.5%. Typically, the microbial oil will have an eicosapentaenoic acid (EPA) content of below 5%, preferably below 1% and more preferably below 0.5%. The oil may have less than 5%, less than 2%, less than 1% of each of $C_{20}$, $C_{20:3}$, $C_{22:0}$ and/or $C_{24:0}$ polyunsaturated fatty acid (PUFAs). The free fatty acid (FFA) content may be #0.4, 0.2 or 0.1%.

Of the triglycerides, preferably at least 40%, such as least 50%, and more preferably at least 60% of the PUFAs present are at the α-position of the glycerol (present in the triglyceride backbone) also known at the 1 or 3 position. It is preferred that at least 20%, such as least 30%, more preferably at least 40% of the PUFA(s) is at the β(2) position.

The phospholipid content of the oil is suitably at a maximum of 5%, 3% or 2% and/or may be at a minimum of from 0.1, 0.5 or 1.0%.

Typically the microbial oil will be one obtainable by the process of the first aspect invention. Preferably the oil will have been isolated from a fungus, more preferably the oil is isolated from *Mortierella* and in particular from *M. alpina*. The oil is suitably hexane extracted.

ARA Content

Purely for the sake of clarity, the calculation of the percentage ARA content will be explained, especially as the literature can, on occasions, calculate the ARA content on a different basis. The percentage of ARA is based on the oil (that has been extracted from the biomass), and not the biomass itself. It is on a weight by weight basis. It is based on an oil extracted by hexane, and is therefore based on hexane extractable lipids (HEL). It is based on the total amount of oil, and not on the total amount of fatty acids (which can sometimes give a misleading higher FIGURE). The ARA content is determined by the well-known FAME analytical protocol (using the fatty acid methyl esters), detailed in AOCS Cel b89. Different solvents will extract different lipids. Note that in the present case, the oil is first extracted with hexane, and then the ARA content of the oil determined by FAME analysis. This will give a different result from first esterifying the arachidonic acid (e.g. while still in the cells) and then extracting the resulting methyl esters for further analysis.

Peroxide Value (POV)

Preferably the POV of the microbial oil is no more than 3.0, 2.5 or 2.0. However, much lower POV values can be obtained using the process of invention, and these values may be less than 1.5 or less than 1.0. Values less than 0.8 and even less than 0.4 can be obtained.

Anisidine Value (AnV)

Preferably the anisidine value of the microbial oil is no more than 1.0, for example no more than 0.6, 0.3 or even no more than 0.1.

Uses and Products

A third aspect of the invention relates to a composition comprising the oil of the second aspect, and where appropriate one or more (additional) substances. The composition may be a foodstuff and/or a food supplement for animals or humans. In embodiments of the invention which are for human consumption the oils may be rendered suitable for human consumption, typically by refining or purification of the oil obtained from the microbes.

The composition may be infant formula or (human) foodstuffs. Here the composition of the formula may be adjusted so it has a similar amount of lipids or PUFAs to normal breast milk. This may involve blending the microbial oil of the invention with other oils in order to attain the appropriate composition.

The composition may be an animal or marine feed composition or supplement. Such feeds and supplements may be given to any farm animals, in particular sheep, cattle and poultry. In addition, the feeds or supplements may be given to farmed marine organisms such as fish and shell fish. The composition may thus include one or more feed substances or ingredients for such an animal.

The oil of the invention may be sold directly as oil and contained in appropriate packaging, typically one piece aluminium bottles internally coated with epoxy phenolic lacquer, and flushed with nitrogen. The oil may contain one or more antioxidants (e.g. tocopherol, vitamin E, palmitate) each for example at a concentration of from 50 to 800 ppm, such as 100 to 700 ppm.

Suitable compositions can include pharmaceutical or veterinary compositions, e.g. to be taken orally or cosmetic compositions. The oil may be taken as such, or it may be encapsulated, for example in a shell, and may thus be in the form of capsules. The shell or capsules may comprise gelatine and/or glycerol. The composition may contain other ingredients, for example flavourings (e.g. lemon or lime flavour) or a pharmaceutically or veterinary acceptable carrier or excipient.

Preferred features and characteristics of one aspect of the invention are equally applicable to another aspect *mutatis mutandis*.

The following Examples are provided to merely illustrate the invention, and are not to be construed to be limiting.

Comparative Examples 1 and 2 and Examples 3 and 4

Production of Arachidonic Acid (ARA)

One 1 ml vial of suspension *Mortierella alpina* strain CBS 168.95 (deposited by DSM N.V., 2600 MA Delft, The Netherlands (who has authorized the present applicant to refer to this deposited biological material) at Centraal Bureau voor Schimmelcultures (CBS), P.O. Box 85167, 3508 AD Utrecht, The Netherlands, on 20 Feb. 1995 under deposit no. DS 30340) was stored at −80° C. and opened aseptically. The contents were used to inoculate a 500 ml flask with 100 ml of a medium containing (g/l):

glucose, 20;

yeast extract (Gistex® paste (solids 80%, protein (Nx6.25) 46%, NaCl 16%, pH (2% solution) 5.6, ash 22%, total plate count $10^4$/g, *Enterobacteriaceae*<10/g, *E. coli*<1/g, yeast and moulds<100/g, available from DSM N.V., Savory Ingredients PO Box 1, 2600 MA Delft), 12.5;

antifoam (Basildon 86/013K silicon/non-silicone antifoam compound used according to manufacturer's instructions, Basildon Chemical Company, Kimber Road, Abingdon, Oxford, England OX14 IRZ), 0.2.

The pH of the medium was adjusted to 7.0 before autoclaving.

The culture was grown at 25° C. for 48 hrs with shaking at 250 rpm and used for the inoculation of four 2000 ml-flasks with 500 ml of a medium containing (g/l): glucose, 20; yeast extract (Gistex® paste), 25; antifoam (Basildon 86/013K), 0.2. The pH before sterilization was 7.0.

These cultures were grown at 25° C. for 24 hrs and used for seeding a 5 $m^3$ inoculation fermentor containing 2400 litres medium of the same composition as used in the 2000 ml-flasks (the pH before sterilization was 6.0).

The fermentation temperature was set at 25° C., agitation at 150 rpm, vessel pressure at 0.5 bar and aeration rate at 0.5 VVM.

The culture from the inoculum fermenter was transferred to the main fermenter after approx. 36 hours (the oxygen uptake rate was >3 mmol/kg/h).

The main fermentor contained (g/l):

glucose, 35;

yeast extract (Expresa 2200® powder, low sodium brewer's yeast, peptone (extract), solids>96%, total N>10%, amino N 6-7%, NaCl<1%, pH (2% solution 5.3-6.3), ash<12.5%, homogenous powder available from DSM N.V., Savory Ingredients), 5.0;
$NaH_2PO_4.2H_2O$, 1.0;
$KH_2PO_4$, 2.0;
$MgSO_4.7H_2O$ 0.5;
Basildon 86/013K, 0.3; citric acid. $1H_2O$, 0.6;
$ZnCl_2$, 0.010;
$Fe_2(SO_4)_3$ 20% $H_2O$, 0.025;
$MnSO_4.1H_2O$, 0.010; (pH before sterilization 5.0).
The glucose was sterilized separately and added to the main fermentor after sterilization.

The fermentation lasted for 175 hours. The pH of the medium was continued at about pH 6 (+/−0.1) with an aeration (air flow) of 0.5 VVM, the air pressure at 0.8 bar and agitation at 70 rpm. Oxygen level was maintained at D.O.≥30% by sequentially increasing agitation speed to 100 rpm and airflow to 0.9 VVM.

A sterile glucose solution of about 50% (w/w) was fed to the fermentor to maintain the glucose concentration to above 10 g/l and from about 30 to 78 hrs 625 kg of a 25% yeast extract solution was fed to the fermentor with a feed rate controlled in such a way that the ammonia concentration was <30 mg/l.

The experiment was performed four times (Examples 1 to 4), and the glucose concentration of the culture medium was monitored over time. A graph of glucose concentration, in g/kg, is shown in FIG. 1, against the number of hours into fermentation. This shows the last value of Example 4 was 2.2 g/kg at 172 hours. This was three hours before the end of fermentation (EoF). The glucose level was zero at about one hour before EoF.

In Comparative Examples 1 and 2 the concentration of the carbon source (glucose) was well above 5 g/kg at the end of fermentation. Indeed, at 10 hours before EoF, the glucose concentration was about 20 g/kg. Thus, in Examples 1 and 2, the concentration of glucose was such that it was not limiting on the group of the micro-organisms, or on the production of ARA.

In Examples 3 and 4 the glucose concentration in the last stage of fermentation, immediately preceding EoF, was controlled in such a way in that about 10 hours before the EoF the concentration of glucose was about 5 g/kg. During this last stage, over 10 hours, the glucose was added at an addition rate of 0.5 g/kg/hr. The glucose concentration was virtually zero at EoF. During this period the consumption rate of the glucose was about twice the rate of addition, namely about 1 g/kg/hr.

The concentration of glucose (g/kg) in the culture medium over time, during fermentation is shown in Tables 1 to 4 (which correspond to Examples 1 to 4).

TABLE 1

| Time (hrs) | Glucose concentration g/kg |
|---|---|
| 0 | 48.7 |
| 24 | 57.6 |
| 28 | 47.8 |
| 54 | 46.4 |
| 78 | 62.0 |
| 102 | 62.5 |
| 126 | 48.2 |
| 150 | 42.5 |
| 167 | 20 |

TABLE 2

| Time (hrs) | Glucose concentration g/kg |
|---|---|
| 0 | 47.8 |
| 28 | 32.5 |
| 54 | 32.2 |
| 78 | 41.3 |
| 102 | 49.5 |
| 126 | 46.8 |
| 150 | 29.9 |
| 165 | 17.1 |

TABLE 3

| Time (hrs) | Glucose concentration g/kg |
|---|---|
| 0 | 49.2 |
| 28 | 60.1 |
| 54 | 40.8 |
| 78 | 34.0 |
| 102 | 37.3 |
| 126 | 23.2 |
| 150 | 16.7 |
| 172 | 7 |

TABLE 4

| Time (hrs) | Glucose concentration g/kg |
|---|---|
| 0 | 45 |
| 28 | 34.1 |
| 54 | 34.7 |
| 78 | 29.2 |
| 102 | 38.1 |
| 126 | 45 |
| 150 | 23.5 |
| 172 | 2.2 |

At the end of fermentation, the micro-organisms and surrounding aqueous liquid (the fermentation broth) was removed from the fermenter. The broth underwent solid liquid separation to remove some of the water. The remaining cells were then extruded, and subjected to solvent-extraction using hexane. An ARA containing microbial oil (hexane extractable lipids) was thus obtained from cells undergoing each of the four different fermentation protocols.

The percentage ARA content of the oil (on a weight by weight basis) was then determined using the well-known FAME analytical protocol (as detailed in AOCS Celb89). In Example 3 the concentration of ARA in the microbial oil was 508 g/kg (50.8%). The equivalent FIGURE for Example 4 was 545 g/kg (54.5% ARA). By comparison, the microbial oil extracted from the cells in Comparative Examples 1 and 2 was much lower at 36.8% and 36.7%, respectively.

We claim:

1. A fermentation process for production of a microbial oil comprising at least 40% arachidonic acid (ARA), the process comprising culturing a microorganism which is *Mortierella alpina* in a two-stage process in a culture medium inside a fermentation vessel, whereby at a second stage of the fermentation process
    (a) a carbon source is rate limiting on the growth of the microorganism,
    (b) the carbon source is restricted such that the microorganism metabolises fat(s) and/or lipid(s) in preference to arachidonic acid (ARA), (c) the carbon source is consumed by the microorganism at a rate greater than it is added to the medium,
(d) the carbon source is added at an addition rate of 0.5 g/kg/hr, and
(e) the carbon source is controlled so that the concentration of the carbon source is about 5 g/kg of medium about 10 hours before the end of fermentation;
whereby the process further comprises extracting the oil from the micro-organism using a non-polar solvent, and wherein the oil has a triglyceride content of at least 90%.

2. The process according to claim 1, wherein: concentration of the carbon source in the second stage is on average ≤0.17M carbon/kg medium.

3. The process according to claim 1, wherein fermentation is carried out at a temperature ≥22° C. and ≤30° C.

4. The process according to claim 1, wherein the carbon source is glucose.

5. The process according to claim 1, wherein during an earlier stage of fermentation, the carbon source is being added, wherein the earlier stage is prior to the second stage.

6. The process according to claim 5, wherein during said earlier stage the carbon source is in excess.

7. The process according to claim 1, wherein cells of the microorganism are pasteurized after fermentation is finished.

8. The process according to claim 1, wherein the oil comprises at least 50% ARA (wt/wt) based on the oil.

9. The process according to claim 1, wherein a concentration of the carbon source in said second stage is <4 g/kg of medium.

10. The process according to claim 1, wherein the solvent is hexane.

11. The process according to claim 8, wherein: concentration of the carbon source in the second stage is on average ≤0.17 M carbon/kg medium.

12. The process according to claim 8, wherein fermentation is carried out at a temperature ≥22° C. and ≤30° C.

13. The process according to claim 1, wherein a concentration of the carbon source in said second stage is <4 g/kg of medium.

14. The process according to claim 8, wherein the carbon source is glucose.

15. The process according to claim 8, wherein during an earlier stage of fermentation, the carbon source is being added, wherein the earlier stage is prior to the second stage.

16. The process according to claim 15, wherein during said earlier stage the carbon source is in excess.

17. The process according to claim 8, wherein the solvent is hexane.

18. The process according to claim 8, wherein cells from the microorganism are pasteurized after fermentation is finished.

* * * * *